(12) United States Patent
Wang et al.

(10) Patent No.: US 10,208,146 B2
(45) Date of Patent: Feb. 19, 2019

(54) CATALYST COMPONENT FOR OLEFIN POLYMERIZATION AND APPLICATION THEREOF

(71) Applicant: Beijing Lihe Technology Ltd., Beijing (CN)

(72) Inventors: Zhiwu Wang, Beijing (CN); Shuhang Li, Beijing (CN); Huashu Li, Beijing (CN); Junwei Zhang, Beijing (CN); Shubin Li, Beijing (CN); Jinsong Dai, Beijing (CN); Qingli Ma, Beijing (CN); Hao Chen, Beijing (CN); Lige Li, Beijing (CN); Wei Bai, Beijing (CN); Fengyao Lei, Beijing (CN)

(73) Assignee: Beijing Lihe Technology Ltd., Beijing (CN)

( * ) Notice: Subject to any disclaimer, the term of this patent is extended or adjusted under 35 U.S.C. 154(b) by 0 days.

(21) Appl. No.: 15/630,801

(22) Filed: Jun. 22, 2017

(65) Prior Publication Data

US 2017/0283530 A1    Oct. 5, 2017

Related U.S. Application Data

(63) Continuation of application No. 15/033,103, filed as application No. PCT/CN2014/076952 on May 7, 2014.

(51) Int. Cl.
| | |
|---|---|
| *C08F 10/00* | (2006.01) |
| *C08F 110/06* | (2006.01) |
| *C08F 4/649* | (2006.01) |
| *C07C 69/757* | (2006.01) |

(52) U.S. Cl.
CPC .......... *C08F 110/06* (2013.01); *C07C 69/757* (2013.01); *C08F 4/6494* (2013.01); *C07C 2601/10* (2017.05); *C07C 2603/18* (2017.05)

(58) Field of Classification Search
None
See application file for complete search history.

(56) References Cited

U.S. PATENT DOCUMENTS

2014/0275451 A1*  9/2014  Chang .................... C08F 10/00
526/111

* cited by examiner

*Primary Examiner* — Yun Qian
(74) *Attorney, Agent, or Firm* — Yong Chen

(57) ABSTRACT

Provided is a solid catalyst component for olefin polymerization, which comprises Mg, Ti, a halogen and an electron donor. The electron donor is selected from at least one of ring-substituted ether-acid ester compounds of the general formula (I). Also provided are a catalyst containing the solid catalyst component and the application of the catalyst in reactions of olefin polymerization, particularly in the reaction of propylene polymerization.

1 Claim, No Drawings

CATALYST COMPONENT FOR OLEFIN POLYMERIZATION AND APPLICATION THEREOF

CROSS REFERENCE TO RELATED APPLICATIONS

This application is continuation of U.S. patent application Ser. No. 15/033,103, filed Apr. 28, 2016, which is a national stage application under 35 U.S.C. 371 based on and claiming the benefit of International Application No. PCT/CN2014/076952, filed on May 7, 2014, which in turn claims the benefit of priority from Chinese Application No. 201310534001.X, filed Oct. 31, 2013. The entire disclosure of each of the prior applications is incorporated herein by reference.

TECHNICAL FIELD

The present invention relates to a solid catalyst component for $CH_2$=CHR olefin polymerization, where R is hydrogen or hydrocarbon group having 1 to 12 carbon atoms, and more particularly, the present invention relates to a solid catalyst component containing at least one particular type of ring-substituted ether-acid ester compound, a catalyst containing the solid catalyst component and the application of the catalyst in reactions of olefin polymerization, particularly in the reactions of propylene polymerization.

BACKGROUND ART

Electron donor compounds can maximally change the property of the active center of Ziegler-Natta catalysts for olefin polymerization, thereby changing the performance of the catalyst to the greatest extent. Therefore, in a sense, research on high-efficiency Ziegler-Natta catalyst is to find better electron donors. The research on the internal electron donor in China and abroad is mainly focused on traditional fatty acid esters and aromatic acid ester compounds; diethers (e.g. EP0361493, EP0728724) and succinic acid esters (e.g. WO9856834, WO0063261, WO03022894) compounds; and diol esters (e.g. CN1580033, CN1580034, CN1580035) compounds, etc. However, in practical applications, there are some problems with the aforementioned compounds serving as the electron donor of catalyst component for olefin polymerization, e.g. the polymers obtained by use of the catalyst system prepared by diether compounds have a narrow molecular weight distribution, while the polymer products obtained by use of the succinic acid ester catalyst system have a broad molecular weight distribution. The activity of diol esters catalyst system is often not as good as that of diether system. In order to obtain a more balanced overall performance of the catalyst, a variety of new compounds have been developed and used in the preparation of Ziegler-Natta catalysts.

Introduction of more functional groups into a compound structure is one of the general trend in creating the electron donor compounds with excellent overall performance. There are many reports on the preparation and application of the polyfunctional compounds, such as the development of new internal electron donor, such as keto-ether (WO2010144079), keto-ester (WO2005097841), and ether-ester (WO2005123784, WO2012087522, WO2012087527). The main purpose of introducing multiple functional groups in a compound is to take full use of the advantages of these functional groups.

However, Ziegler-Natta catalyst components prepared by using the aforementioned compounds are still unsatisfactory in activity/isotacticity when used for olefin polymerization, therefore further research and development are still required.

SUMMARY OF THE INVENTION

The object of the present invention is to provide a solid catalyst component for $CH_2$=CHR olefin polymerization.

Another object of the present invention is to provide a method for preparing the solid catalyst component.

A further object of the present invention is to provide uses of the catalyst component in preparation of a catalyst for $CH_2$=CHR olefin polymerization.

To attain the object of the present invention, provided is a solid catalyst component for olefin polymerization (olefin $CH_2$=CHR, where R is hydrogen or hydrocarbon group having 1 to 12 carbon atoms), which comprises Mg, Ti, a halogen and an electron donor. The electron donor is selected from at least one of ring-substituted ether-acid ester compounds represented by the general formula (I) below:

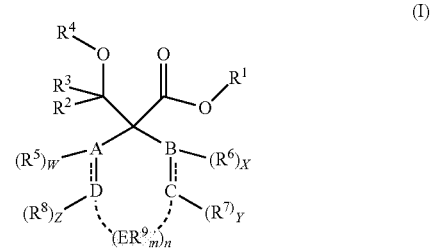

wherein, A, B, C, D, and E are each carbon atoms, or are selected from N, O and S heteroatoms; W, X, Y, Z, and m are each 0, 1 or 2; with the proviso that when n is equal to 0:

I) B is a nitrogen atom, A, C and D are each carbon atoms, X is 1, W, Y and Z are each 2; or II) C is a nitrogen atom, A, B and D are each carbon atoms, Y is 1, W, X and Z are each 2; or III) C is an oxygen atom, A, B, and D are each carbon atoms, Y is 0, W, X and Z are each 2; or IV) A and C are each oxygen atoms, W and Y are each 0, X and Z are each 2; or V) B is an oxygen atom, A, C and D are each carbon atoms, X is 0, W, Y and Z are each 2; or VI) A, B, C and D are each carbon atoms and bonded to each other through a single bond, W, X, Y and Z are each 2; or VII) A, B, C and D are each carbon atoms, B and C are bonded through a double bond, X and Y are each 1, W and Z are each 2; or VIII) A, B, C and D are each carbon atoms, A and D, B and C, respectively, are bonded through a double bond, W, X, Y and Z are each 1;

when n is equal to 1:

i) D is a nitrogen atom, A, B, C, and E are each carbon atoms, Z is 1, W, X, Y, and m are each 2; or ii) E is a nitrogen atom, A, B, C and D are each carbon atoms, m is 1, W, X, Y and Z are each 2; or iii) E is an oxygen atom, A, B, C and D are each carbon atoms, m is 0, W, X, Y and Z are each 2; or iv) C and D are each oxygen atoms, A, B and E are each carbon atoms, Y and Z are each 0, W, X, and m are each 2; or v) D is an oxygen atom, A, B, C, and E are each carbon atoms, Z is 0, W, X, Y, and m are each 2; or vi) B is an oxygen atom, A, C, D, and E are each carbon atoms, X is 0, W, Y, Z, and m are each 2;

vii) A, B, C, D, and E are each carbon atoms, W, X, Y, Z, and m are each 2;

viii) A, B, C, D, and E are each carbon atoms, B and C are bonded through a double bond, X and Y are each 1, W, Z, and m are each 2; or ix) A, B, C, D, and E are each carbon atoms, A and D, B and C, respectively, are bonded through a double bond, W, X, Y and Z are each 1, m is 2;

when n is equal to 2:

A and B are each carbon atoms, W and X are each 2, C and D are each a carbon atom, sulfur atom, oxygen atom or nitrogen atom, Y and Z are each 2 or 0, E represents two carbon atoms bonded through a single bond or a double bond, where when the two carbon atoms of E are bonded through a double bond, m is equal to 1, and when the two carbon atoms of E are bonded through a single bond, m is equal to 2;

$R^1$ and $R^4$ are same or different $C_1$-$C_{20}$ hydrocarbon groups, such as $C_1$-$C_{20}$ linear or branched alkyl, alkenyl, $C_3$-$C_{20}$ cycloalkyl, $C_6$-$C_{20}$ aryl, $C_7$-$C_{20}$ alkaryl and $C_7$-$C_{20}$ aralkyl group; $R^2$, $R^3$, $R^5$-$R^9$ are same or different, and are each selected from a hydrogen atom, halogen atom, oxygen atom, sulfur atom and $C_1$-$C_{20}$ hydrocarbon group, such as $C_1$-$C_{20}$ linear or branched alkyl, $C_3$-$C_{20}$ cycloalkyl, $C_6$-$C_{20}$ aryl, $C_7$-$C_{20}$ alkaryl and $C_7$-$C_{20}$ aralkyl group;

Said $R^1$-$R^9$ each may optionally contain one or more R atoms as a substituent of a carbon atom or hydrogen atom, or both, where R is a heteroatom, a linear or branched $C_1$-$C_{20}$ alkyl, $C_3$-$C_{20}$ cycloalkyl, $C_6$-$C_{20}$ aryl, $C_7$-$C_{20}$ alkaryl and $C_7$-$C_{20}$ aralkyl group; wherein any two groups of $R^1$-$R^9$ may be bonded to each other to generate one or more spiro ring or fused ring structures.

The examples of the compounds included in the general formula (I) are listed as follows:

Five-membered ring ether-acid ester compounds:

Ethyl 1-(1,1-vinyl di oxyethyl)cyclopentane-1-carboxylate; ethyl 2-(1-methoxycyclopentane)-2-methoxy acetate; methyl 1-(methoxymethyl)cyclopentane carboxylate; methyl 1-(benzyloxymethyl)cyclohexyl carboxylate; ethyl 1-(4,4,6-trimethyl-[1,3]azapyran-2-yl)-cyclopentyl carboxylate; methyl 2-chloro-methoxyethyl-1-cyclopentyl carboxylate; bi(cyclohexyl carboxylic acid methyl ester)methyl methyl ether; ethyl 2-benzyloxy-(1,1-vinyl di oxyethyl)cyclopentyl carboxylate; dimethyl-1-methoxybicyclo[2.2.2]oct-8-ene-2,6-dicarboxylic acid methyl ester; 1-methoxybicyclo[2.2.2]oct-9-ane, trimethyl-1-methoxybicyclo[2.2.1]heptane-2,6,10-tricarboxylate; 1-methoxy-1-cyclopentane carboxylic acid ethyl ester-3-phenyl-propylene; 2-benzyloxymethyl-2-ethoxycarbonyl-1-(tetrahydropyran-2-oxy)oxocyclopentane; 2-benzyloxy-2-ethoxycarbonyl-cyclopentanol; methyl 1-(1-methoxyethyl)cyclopentane carboxylate; 2-methyl-2-(1-cyclopentyl carboxylic acid ethyl ester-1-yl)-4-methylene-1,3-oxopropane; methyl-(3,4-dihydro-1H-isopyran-1-yl) cyclopentyl carboxylate; ethyl 1-(methoxymethyl)cyclopentane carboxylate; methyl-1-(ethoxymethyl)cyclopentane carboxylate; 2-benzyloxymethyl-1-cyclopentanonecarboxylic acid ethyl ester; methyl 1-benzyloxymethyl-pyrrolidine-2-carboxylate; methyl-hexahydro-2,2,7-trimethyl-6-oxo[1,3]dioxo[5,4-b]pyrrole-4a-carboxylate; methyl-2-benzyloxymethyl-5-carbonylpyrrolidine-2-carboxylate; methyl-1-(4-chlorophenyl)-3-(methoxymethyl)-4,5-dicarbonylpyrrole-3-carboxylate; methyl 3-methoxymethyl-pyrrolidine-3-carboxylate; 1-tert-butoxycarbonylmethyl-3-methoxymethyl-pyrrolidine-3-carboxylate; methyl 1-benzyl-3-methoxymethyl-pyrrolidine-3-carboxylate; 2-ethoxymethyl-pyrrolidine-1,2-dicarboxylic acid 1-tert-butyl ester 2-methyl ester; 2-isopropoxymethyl-pyrrolidine-1,2-dicarboxylic acid 1-tert butyl ester 2-ethyl ester; methyl 3-methoxymethyl-1-(3-methylphenyl)-4,5-dicarbonylpyrrolidine-3-carboxylate; methyl 3-methoxy-1-(4-fluorophenyl)-4,5-dicarbonylpyrrolidine-3-carboxylate; methyl 3-methoxymethyl-1-(4-bromophenyl)-4,5-dicarbonylpyrrolidine-3-carboxylate; methyl 1-(4-hydroxyphenyl)-3-methoxymethyl-4,5-dicarbonylpyrrolidine-3-carboxylate; ethyl 3-ethoxymethyl-1-phenyl-4,5-dicarbonylpyrrolidine-3-carboxylate; ethyl 3-ethoxymethyl-1-(3-methylphenyl)-4,5-dicarbonylpyrrolidine-3-carboxylate; ethyl 3-methoxymethyl-2-carbonyl-tetrahydrofuran-3-carboxylate; ethyl 3-isopropoxymethyl-2-carbonyl-tetrahydrofuran-3-carboxylate; ethyl 1-(4,4,6-trimethyl-[1,3]oxazin-2-yl)-cyclopentyl carboxylate; methyl-3-ethyl-2-[(2-trimethylsilylethoxy) methoxymethyl]1,4-dioxaspiro[4.4]nonane-2-carboxylate; methyl 5-oxo-phenyl-2-deoxy-4-methoxycarbonyl-D-pentofuranoside; 2-benzyloxymethyl-3-(2-methoxyvinyl)-2-methoxycarbonyl-1,4-oxaspiro[4.4]nonane; 4-pentenyl-5-O-benzyl-2-deoxy-4-methoxycarbonyl-D-pentofuranoside; methyl 5-O-benzyl-3-O-(t-butyldimethyl silane)-2-deoxy-4-methoxycarbonyl-D-pentofuranoside; 1-(2-benzyloxymethyl-3-hydroxy-2-methoxycarbonyl-5-tetrahydrofuran)thymine; 4-N-acetyl-1-(2-benzyloxymethyl-3-hydroxy-2-methoxycarbonyl-5-tetrahydrofuran)cytosine; 4-N-acetyl-5-O-benzyl-2-deoxy-4-methoxycarbonyl-cytosine; methyl-3,3-dimethyl-8-[5-methyl-2(1-H), 4-(3H)-dioxopyridine-1-yl]-2,4-dioxabicyclo[4.3.0]non-6-carboxylate; methyl-1-(4-methoxybenzyl)-2-benzyloxymethyl-3-hydroxy-3-methyl-4-methyl ene-5-pyrrolidin-2-carbaldehyde; methyl 2-(hydroxymethoxymethyl)1-methoxy-5-carbonylpyrrolidin-2-carboxylate; ethyl (2-cyclopentyl-[1,3]dioxolan-2-)-1-ethyl-2-oxa-2,3-dihydro-1H-indole-3-carboxylate; benzyloxycarbonyl-thioprolyl-thioproline diethyl acetal; benzyloxycarbonyl-thioprolyl-thioproline dibutyl acetal; benzyloxycarbonyl-thioprolyl-thioproline dimethyl acetal; methyl-2-(benzyloxymethyl)-3-hydroxy-4-methyl ene-5-carbonylpyrrolidine-2-carboxylate; 1-tert-butyl-2-methyl-2-(benzyloxymethyl)-5-oxo-pyrrolidine-1,2-dicarboxylate; methyl-2-benzyloxymethyl-3-tertbutyldimethyl silyl oxy-4-methyl-5-carbonylpyrrolidine-2-carboxylate; 1-tert-butyl-2-methyl-2(benzyloxymethyl)-3-hydroxy-4-methyl ene-5-oxopyrrolidine-1,2-dicarboxylate; 5-tert-butyl-6-methyl-6-(benzyl oxymethyl)-2-methyl-4-oxohexahydro-5H-pyrrolo[3,4-d]oxazole-5,6-dicarboxylate; methyl-1-(3,4-dihydro-1H-isobenzo-1-yl)cyclopentane carboxylate; tert-butyl-1-(1-ethoxy-3-phenyl-allyl)-2-carbonylcyclopentane carboxylate; 1-tert-butyl-2-methyl-2 (benzyl oxymethyl) pyridine-1,2-dicarboxylate; N-(t-butoxycarbonyl)-α-(methoxymethyl) proline ethyl ester; N-(t-butoxycarbonyl)-α-(t-butylmethyl)proline ethyl ester; 1-tert-butyl-2-methyl-2-(benzyloxymethyppyrrolidine-1,2-dicarboxylate; methyl 3-benzyloxymethyl-1-(2,6-dimethylphenyl)-5-oxo-pyrrolidine-3-carboxylate; ethyl 1-benzyl-2-(diethoxymethyl)pyrrolidine-2-carboxylate; methyl 2-benzyloxymethyl-1-methyl-pyrrolidine-2-carboxylate;

9-methoxymethyl-fluorene carboxylic acid-(9)-methyl ester; 9-ethoxymethyl-fluorene carboxylic acid-(9)-methyl ester; 9-methoxymethyl-fluorene carboxylic acid-(9)-ethyl ester; 9-methoxymethyl-fluorene carboxylic acid-(9)-n-butyl ester; 9-methoxymethyl-fluorene carboxylic acid-(9)-isobutyl ester; 9-methoxymethyl-fluorene carboxylic acid-(9)-isopropyl ester; 9-ethoxymethyl-fluorene carboxylic acid-(9)-ethyl ester; 9-ethoxymethyl-fluorene carboxylic acid-(9)-n-butyl ester; 9-ethoxymethyl-fluorene carboxylic acid-(9)-isobutyl ester; 9-ethoxymethyl-fluorene carboxylic acid-(9)-isopropyl ester; bi(9-methoxy carbonyl-fluoren-9-yl)-ether; methyl 3-[1-[2-(indol-3-yl)-1-oxo-ethyl]]-2-methoxy-3-azabicyclo[3.2.1]oct-6-ene-7-ethyl-1-carboxylate; methyl-2-methoxydibenzobicyclo-[3.2.1]octadien-1-carboxylate; methyl-benzyl oxymethyl-2-cyclopent-2-ene-1-carboxylate; methyl-4-[(tert-butoxycarbonyl)amino]-1-ethoxymethyl-cyclopent-2-ene-1-carboxylate; 8-benzyloxy-1-ethoxycarbonyl-5,7,7-trimethyl-2-(propan-2-ylidene) bicyclo[3.3.0]oct-2-ene; methyl-1,1-bis(hydroxymethyl)-3-methoxy-1,2,3,3a,6,6a-hexahydropentene-3a-carboxylate; methyl-1-(t-butyldimethyl siloxymethyl)-1-di(hydroxymethyl)-3-methoxy-1,2,3,3a,6,6a-hexahydropentene-3a-carboxylate; methyl 1,1-bis(benzyl oxymethyl)-3-methoxy-1,2,3,3a,6,6a-hexahydropentene-3a-carboxylate; 1,2,3,4,5-pentamer (methoxycarbonyl)-5-(methoxy methyl) cyclopentadiene;

Six-membered ring ether acid-ester compounds:

Methyl benzyloxymethyl-cyclohexyl carboxylate; ethyl 8-benzyloxymethyl-1,4-dioxo-spiro[4.5]decane-8-carboxylate; 2-benzyloxymethyl-2-ethoxycarbonylcyclohexanol; 2-benzyloxymethyl-2-ethoxycarbonyl-1-(tetrahydrofuran-2-yl)oxacyclohexane; methyl 4-(1,3-dioxolan-2-yl)-(1,1'-dicyclohexyl)-4-carboxylate; ethyl-1-(benzyloxymethyl)-4,4-difluorocyclohexanecarboxylate; ethyl 6-methoxymethyl-1, 4-dioxaspiro[4.5]decane-6-carboxylate; 2-methoxymethyl-2-ethoxycarbonyl-6-methyl cyclohexanol; ethyl 1-di ethoxymethyl-cyclohexyl carboxylate; methyl methoxy-chloromethyl-cyclohexylcarboxylate; spiro[bicyclo[3.3.1] nonane-2,2'-[1.3][1.3]dioxa-2,2'-[1.3]dioxolane]1-butyric acid methyl ester; ethyl 1-benzyloxymethyl-4-dimethoxycyclohexyl-carboxylate; ethyl benzyloxymethyl-4-methoxycyclohexyl-carboxylate; ethyl-4-methyl-1-methoxymethyl-4-trimethylsiloxycyclohexyl carboxylate; methyl 1-methoxymethyl-cyclohexylcarboxylate; methyl 1-(3,4-dihydro-1H-isobenzo-1-yl) cyclopentyl carboxylate; tert-butyl-4-hydroxy-1-(methoxymethyl)cyclohexane carboxylate; tert-butyl-4-(tert-butyldimethylsiloxy)-1-(methoxymethyl) cyclohexane carboxylate; tert-butyl-4-(5-aminopyridine-2-oxy)-1-(methoxymethyl)cyclohexane carboxylate; tert-butyl-1-methoxymethyl-4-(5-nitropyridin-2-oxy) cyclohexanecarboxylate; ethyl 1-(2-methoxyethoxymethyl)-cyclohexyl carboxylate; ethyl 4,4-difluoro-1-(methoxymethyl)cyclohexyl carboxylate; 4-benzyloxymethyl-piperidine-1,4-dicarboxylic acid 1-tert-butyl ester 4-ethyl ester; ethyl 4-benzyloxymethyl-piperidine-4-carboxylate; ethyl 1-((benzyloxymethyl)methyl)2-oxocyclohexane carboxylate; 2-benzyloxymethyl-2-ethoxycarbonyl cyclohexanol; 2-benzyloxymethyl-2-ethoxycarbonyl-1-(tetrahydropyran-2-yl)-oxy-cyclohexane; ethyl 4-methoxymethylpiperidine-4-carboxylate; methyl 5-methoxyethyl-2-phenyl-[1.3]dioxan-5-carboxylate; ethyl 2-oxacyclohexan-oxo-furo-[1.3]dithiane-2-carboxylate; diethyl-3-phenyl-6,6-(ethylenedioxy)-2-oxo-3-azabicyclo [3.3.1]nonane-1,5-dicarboxylate; methyltetrahydro-(3,4-dihydro-1H-isobenzo-1-yl)-2H-pyran-4-carboxylate; methyl-tetrahydro-(3,4-dihydro-1H-isobenzo-1-yl)-2H-pyran-4-carboxylate; methyl 1-(3,4-dihydro-1H-isobenzo-1-yl) cyclohexanecarboxylate; methylenetetrahydro-3,4-dihydro-5-methyl-1H-isobenzo-1-yl)-2H-2-pyran-4-carboxylate; ethyl 4,4-difluoro-1-(methoxymethyl)cyclohexane carboxylate; ethyl 2-(methoxymethyl) tetrahydro-2H-pyran-2-carboxylate; 3-methoxymethyl-3-ethoxycarbonyl-1-methyl-cyclohexen(1); methyl-2,3,3a,4,5,7a-hexahydro-3,3a-dimethyl-1,5-bi-[2-(trimethylethoxysilane-oxy]indene-7a-carboxylate; 1-benzyloxymethyl-1-methoxycarbonyl-2,5-cyclohex ene;

Seven-membered ring ether-ester compounds:

Methyl 4-benzyl-7-methoxy-3-oxo-3,4-dihydro-2H-1,5-benzothia-4-carboxylate; methyl 4-benzyloxymethyl-3-(4-methoxybenzyl)-5-methyl-7-oxo-6-oxa-3-aza-bicyclo [3.2.0]heptane-4-carboxylate.

Preferably, 9-methoxymethyl-fluoren e carboxylic acid-(9)-methyl ester; 9-ethoxymethyl-fluorene carboxylic acid-(9)-methyl ester; 9-methoxymethyl-fluorene carboxylic acid-(9)-ethyl ester; 9-methoxymethyl-fluorene carboxylic acid-(9)-n-butyl ester; 9-methoxymethyl-fluorene carboxylic acid-(9)-isobutyl ester; 9-methoxymethyl-fluorene carboxylic acid-(9)-isopropyl ester; 9-ethoxymethyl-fluorene carboxylic acid-(9)-ethyl ester; 9-ethoxymethyl-fluorene carboxylic acid-(9)-n-butyl ester; 9-ethoxymethyl-fluorene carboxylic acid-(9)-isobutyl ester; 9-ethoxymethyl-fluorene carboxylic acid-(9)-isopropyl ester.

Preferred compounds of general formula (I) include those compounds of formula (II) below:

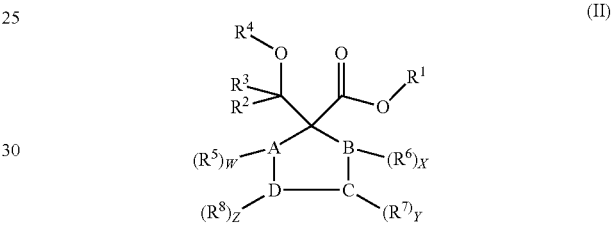

(II)

Wherein A, B, C and D are each carbon atoms, or are selected from N, O and S heteroatoms; W, X, Y and Z are 0, 1 or 2; $R^1$-$R^8$ groups are defined as in the general formula (I), $R^5$-$R^8$ groups are same or different groups.

Preferred compounds of formula (II) include those compounds of formula (III) below:

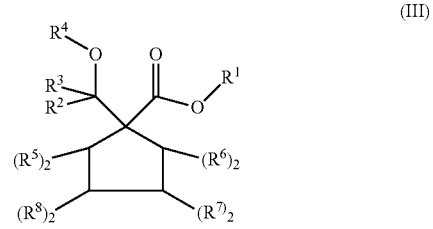

(III)

wherein $R^1$-$R^8$ groups are defined as in the general formula (I), $R^5$-$R^8$ groups are same or different groups.

In the five-membered ring compounds represented by general formula (II) or (III), suitable specific compounds are shown as follows:

Ethyl 1-(1,1-vinyl di oxyethyl)cyclopentane-1-carboxylate; ethyl 2-(1-methoxycyclopentane)-2-methoxy acetate; methyl 1-(methoxymethyl)cyclopentane carboxylate; methyl 1-(benzyloxymethyl)cyclohexyl carboxylate; ethyl 1-(4,4,6-trimethyl-[1,3]azapyran-2-yl)-cyclopentyl carboxylate; methyl 2-chloro-methoxyethyl-1-cyclopentyl carboxylate; bi(cyclohexyl carboxylic acid methyl ester)methyl methyl ether; ethyl 2-benzyloxy-(1,1-vinyl di oxyethyl)cyclopentyl carboxylate; dimethyl-1-methoxybicyclo[2.2.2] oct-8-ene-2,6-dicarboxylic acid methyl ester; 1-methoxybicyclo[2.2.2]oct-9-ane; trimethyl-1-methoxybicyclo[2.2.1]heptane-2,6,10-tricarboxylate; 1-methoxy-1-cyclopentane carboxylic acid ethyl ester-3-phenyl-propylene; 2-benzyloxymethyl-2-ethoxycarbonyl-1-(tetrahydropyran-2-oxy) oxocyclopentane; 2-benzyloxy-2-ethoxycarbonyl-cyclopentanol; methyl 1-(1-methoxyethyl)cyclopentane carboxylate; 2-methyl-2-(1-cyclopentyl carboxylic acid ethyl ester-1-yl)-4-methyl ene-1,3-oxopropane; methyl-(3,4-dihydro-1H-isopyran-1-yl) cyclopentyl carboxylate; ethyl 1-(methoxymethyl)cyclopentane carboxylate; methyl-1-(ethoxymethyl) cyclopentane carboxylate; 2-benzyloxymethyl-1-cyclopentanonecarboxylic acid ethyl ester; methyl 1-benzyloxymethyl-pyrrolidine-2-carboxylate; methyl-hexahydro-2,2,7-trimethyl-6-oxo[1,3]dioxo[5,4-b]pyrrole-4a-carboxylate; methyl-2-benzyloxymethyl-5-carbonylpyrrolidine-2-carboxylate; methyl-1-(4-chlorophenyl)-3-(methoxymethyl)-4,5-dicarbonylpyrrole-3-carboxylate; methyl 3-methoxymethyl-pyrrolidine-3-carboxylate; 1-tert-butoxycarbonylmethyl-3-methoxymethyl-pyrrolidine-3-carboxylate; methyl 1-benzyl-3-methoxymethyl-pyrrolidine-3-carboxylate; 2-ethoxymethyl-pyrrolidine-1,2-dicarboxylic acid 1-tert-butyl ester 2-methyl ester; 2-isopropoxymethyl-pyrrolidine-1,2-dicarboxylic acid 1-tert butyl ester 2-ethyl ester; methyl 3-methoxymethyl-1-(3-methylphenyl)-4,5-di carbonylpyrrolidine-3-carboxylate; methyl 3-methoxy-1-(4-fluorophenyl)-4,5-di carbonylpyrrolidine-3-carboxylate; methyl 3-methoxymethyl-1-(4-bromophenyl)-4,5-di carbonylpyrrolidine-3-carboxylate; methyl 1-(4-hydroxyphenyl)-3-methoxymethyl-4,5-di carbonylpyrrolidine-3-carboxylate; ethyl 3-ethoxymethyl-1-phenyl-4,5-dicarbonylpyrrolidine-3-carboxylate; ethyl 3-ethoxymethyl-1-(3-methylphenyl)-4,5-di carbonyl pyrrolidine-3-carboxylate; ethyl 3-methoxymethyl-2-carbonyl-tetrahydrofuran-3-carboxylate; ethyl 3-isopropoxymethyl-2-carbonyl-tetrahydrofuran-3-carboxylate; ethyl 1-(4,4,6-trimethyl-[1,3]oxazin-2-yl)-cyclopentyl carboxylate; methyl-3-ethyl-2-[(2-trimethylsilylethoxy) methoxymethyl]1,4-dioxaspiro[4.4]nonane-2-carboxylate; methyl 5-oxo-phenyl-2-deoxy-4-methoxycarbonyl-D-pentofuranoside; 2-benzyloxymethyl-3-(2-methoxyvinyl)-2-methoxycarbonyl-1,4-oxaspiro[4.4]nonane; 4-pentenyl-5-O-benzyl-2-deoxy-4-methoxycarbonyl-D-pentofuranoside; methyl 5-O-benzyl-3-O-(t-butyldimethyl silane)-2-deoxy-4-methoxycarbonyl-D-pentofuranoside; 1-(2-benzyloxymethyl-3-hydroxy-2-methoxycarbonyl-5-tetrahydrofuran)thymine; 4-N-acetyl-1-(2-benzyloxymethyl-3-hydroxy-2-methoxycarbonyl-5-tetrahydrofuran)cytosine; 4-N-acetyl-5-O-benzyl-2-deoxy-4-methoxycarbonyl-cytosine; methyl-3,3-dimethyl-8-[5-methyl-2(1-H), 4-(3H)-dioxopyridine-1-yl]-2,4-dioxabicyclo[4.3.0]non-6-carboxylate; methyl-1-(4-methoxybenzyl)-2-benzyloxymethyl-3-hydroxy-3-methyl-4-methyl ene-5-pyrrolidin-2-carb aldehyde; methyl 2-(hydroxymethoxymethyl)1-methoxy-5-carbonylpyrrolidin-2-carboxylate; ethyl (2-cyclopentyl-[1,3]dioxolan-2-)-1-ethyl-2-oxa-2,3-dihydro-1H-indole-3-carboxylate; benzyloxycarbonyl-thioprolyl-thioproline diethyl acetal; benzyloxycarbonyl-thioprolyl-thioproline dibutyl acetal; benzyloxycarbonyl-thioprolyl-thioproline dimethyl acetal; methyl-2-(benzyloxymethyl)-3-hydroxy-4-methyl ene-5-carbonylpyrrolidine-2-carboxylate; 1-tert-butyl-2-methyl-2-(benzyloxymethyl)-5-oxo-pyrrolidine-1,2-dicarboxylate; methyl-2-benzyloxymethyl-3-tertbutyldimethyl silyl oxy-4-methyl-5-carbonylpyrrolidine-2-carboxylate; 1-tert-butyl-2-methyl-2(benzyloxymethyl)-3-hydroxy-4-methyl ene-5-oxopyrrolidine-1,2-dicarboxylate; 5-tert-butyl-6-methyl-6-(benzyl oxymethyl)-2-methyl-4-oxohexahydro-5H-pyrrolo [3,4-d]oxazole-5,6-dicarboxylate; methyl-1-(3,4-dihydro-1H-isobenzo-1-yl)cyclopentane carboxylate; tert-butyl-1-(1-ethoxy-3-phenyl-allyl)-2-carbonylcyclopentane carboxylate; 1-tert-butyl-2-methyl-2 (benzyloxymethyl) pyridine-1,2-dicarboxylate; N-(t-butoxycarbonyl)-α-(methoxymethyl) proline ethyl ester; N-(t-butoxycarbonyl)-α-(t-butylmethyl)proline ethyl ester; 1-tert-butyl-2-methyl-2-(benzyloxymethyppyrrolidine-1,2-dicarboxylate; methyl 3-benzyloxymethyl-1-(2,6-dimethylphenyl)-5-oxo-pyrrolidine-3-carboxylate; ethyl 1-benzyl-2-(diethoxymethyl)pyrrolidine-2-carboxylate; methyl 2-benzyloxymethyl-1-methyl-pyrrolidine-2-carboxylate;

The compounds of the general formula (I) further preferably comprise the compounds of the following general formula (IV):

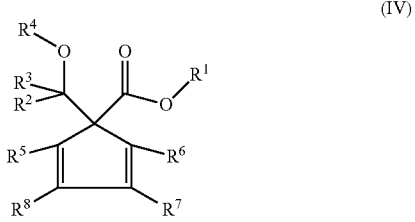

(IV)

wherein $R^1$-$R^8$ groups are defined as in the general formula (I).

More preferred compounds are the compounds of the general formula (V):

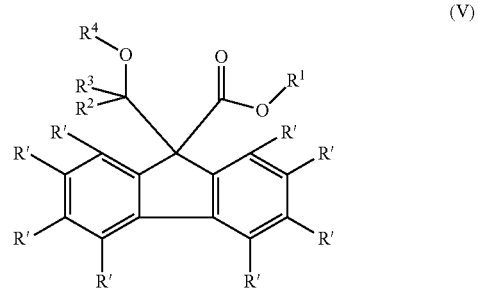

(V)

wherein $R^1$-$R^4$ groups are defined as in the general formula (I), R' is same or different hydrogen, halogen atom, linear or branched $C_1$-$C_{20}$ alkyl, $C_3$-$C_{20}$ cycloalkyl, $C_6$-$C_{20}$ aryl, $C_7$-$C_{20}$ alkaryl and $C_7$-$C_{20}$ aralkyl group.

In the five-membered ring compounds represented by general formula (IV) or (V), suitable specific compounds are shown as follows:

9-methoxymethyl-fluorene carboxylic acid-(9)-methyl ester; 9-ethoxymethyl-fluorene carboxylic acid-(9)-methyl ester; 9-methoxymethyl-fluorene carboxylic acid-(9)-ethyl ester; 9-methoxymethyl-fluorene carboxylic acid-(9)-n-butyl ester; 9-methoxymethyl-fluorene carboxylic acid-(9)-isobutyl ester; 9-methoxymethyl-fluorene carboxylic acid-(9)-isopropyl ester; 9-methoxymethyl-fluorene carboxylic acid-(9)-benzyl ester; 9-ethoxymethyl-fluorene carboxylic acid-(9)-ethyl ester; 9-ethoxymethyl-fluorene carboxylic acid-(9)-benzyl ester; 9-ethoxymethyl-fluorene carboxylic acid-(9)-n-butyl ester; 9-ethoxymethyl-fluorene carboxylic acid-(9)-isobutyl ester; 9-ethoxymethyl-fluorene carboxylic acid-(9)-isopropyl ester; 9-methoxybenzyl-fluorene carboxylic acid (9)-benzyl ester; bi(9-methoxy carbonyl-fluoren-9-yl)-ether; 1,2,3,4,5-pentamer (methoxycarbonyl)-5-(methoxy methyl)cyclopentadiene;

Preferred compounds from the above include 9-methoxymethyl-fluorene carboxylic acid-(9)-methyl ester; 9-ethoxymethyl-fluorene carboxylic acid-(9)-methyl ester;

9-methoxymethyl-fluorene carboxylic acid-(9)-ethyl ester; 9-methoxymethyl-fluorene carboxylic acid-(9)-n-butyl ester; 9-methoxymethyl-fluorene carboxylic acid-(9)-isobutyl ester; 9-methoxymethyl-fluorene carboxylic acid-(9)-isopropyl ester; 9-ethoxymethyl-fluoren e carboxylic acid-(9)-ethyl ester; 9-ethoxymethyl-fluorene carboxylic acid-(9)-n-butyl ester; 9-ethoxymethyl-fluorene carboxylic acid-(9)-isobutyl ester; 9-ethoxymethyl-fluorene carboxylic acid-(9)-isopropyl ester.

The ring-substituted ether-acid esters of the present invention can be synthesized by a variety of reaction schemes. One of them includes a three-step reactions that comprises: a cyclic hydrocarbon-substituted carboxylic acid is prepared from the corresponding ring-substituted compound, and then reacted with the corresponding alcohol $R^1OH$ to form a formate by esterification, or with a suitable ester precursor to directly form a cyclic hydrocarbon-substituted formate by addition; the product of the above step is reacted with a suitable alkoxy group-containing precursor by addition to obtain the final product.

Specifically: Step A is to react a corresponding ring-substituted compound with carbon dioxide and alkyl lithium reagent, or with alkyl dimethyl ester and sodium hydride to obtain a cyclic hydrocarbon substituted carboxylic acid (see U.S. Pat. No. 4,564,700A1);

Step B is to react the product of Step A with the corresponding alcohol $R^1OH$ to form a formate by esterification, or with a suitable ester precursor to directly form a cyclic hydrocarbon-substituted formate by addition (see Journal of the Chemical Society, 1949, P 2182, 2185);

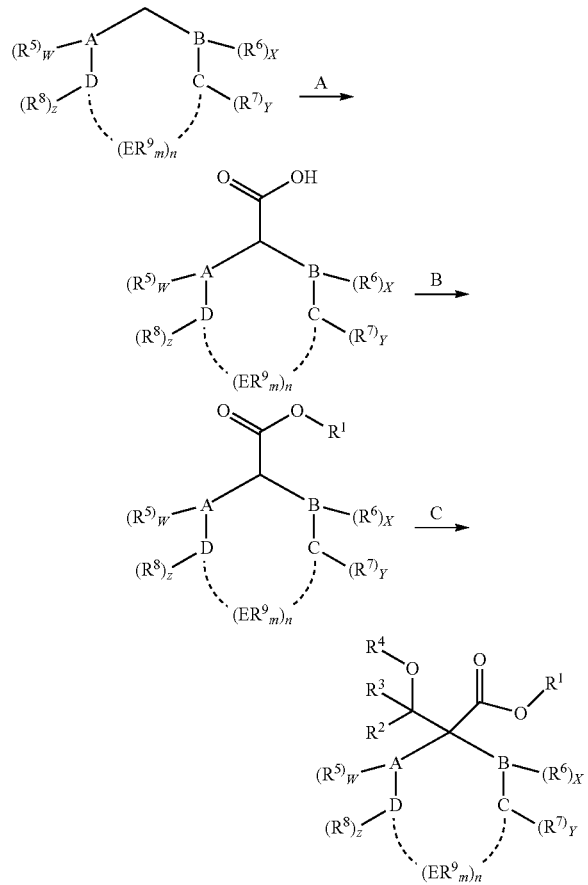

Step C is to react the product of step B with a suitable hydrocarboxy precursor by addition to obtain the final product (see Analytical Chemistry, 32 vol, NO. 4, April 1960).

The order of Step A and Step C in the above preparation process can be reversed, i.e. the ether group can be added first, and then the carboxylic acid (ester) group.

The solid catalyst component for olefin polymerization of the present invention comprises the reaction product of a titanium compound, a magnesium compound and a ring-substituted ether-acid ester compound selected from the general formula (I)-(V), the precursor of said magnesium compound is selected from at least one of: $RMgX$, $MgR_2$, $MgCl_2 \cdot mROH$, $Mg(OR)_2$, $X_nMg(OR)_{2-n}$, $MgCl_2/SiO_2$ or mixture of magnesium halide and titanium alkoxide, wherein m is a number from 0.1 to 6, 0<n<2, X is halogen, R is $C_1$-$C_{20}$ hydrocarbon group; said titanium compound is represented by general formula $TiX_n(OR)_{4-n}$, wherein R is $C_1$-$C_{20}$ hydrocarbon group, X is halogen, n=1-4.

Preferred magnesium compounds of the present invention are magnesium hydrocarboxide compounds.

Other preferred magnesium compounds of the present invention are alcoholates of magnesium dihalide.

Yet other preferred magnesium compounds of the present invention are liquid magnesium compounds.

The titanium compounds of the invention include titanium tetrachloride, titanium tetrabromide, titanium tetraiodide and alkoxy titanium halide, alkyl titanium halide such as methoxy titanium trichloride, ethoxy titanium trichloride, propoxy titanium trichloride, n-butoxy titanium trichloride, dimethoxy titanium dichloride, diethoxy titanium dichloride, dipropoxy titanium dichloride, di-n-butoxy dichloride titanium, trimethoxy titanium chloride, triethoxy titanium chloride, tripropoxy titanium chloride or tri-n-butoxy titanium chloride. These titanium halides can be used alone or in combination. Titanium tetrachloride is preferably used.

Solid catalyst component of the present invention can be prepared in various ways.

According to one way of preparation, a solution of $TiCl_4$ or titanium alkoxide in an aromatic hydrocarbon (e.g., toluene, xylene, etc.), is reacted with magnesium dihydrocarboxide such as magnesium dialkoxide or magnesium diaryloxide or the like at −25-0° C., and halogenated at 80-130° C. Treatment with solution of $TiCl_4$ in an aromatic hydrocarbon can be repeated one or more times and the ring-substituted ether-acid ester compounds of the general formula (I)-(V) can be added in such treatments. For example, it may be prepared according to the preparation method of titanium-containing solid catalyst component as disclosed in U.S. Pat. No. 5,077,357: successively adding magnesium ethoxide, titanium tetraethoxide, o-cresol, ethanol and chlorobenzene with stirring; quickly adding $TiCl_4$/chlorobenzene solution to the above liquid, heating the mixture until complete dissolution, continuing to heat the mixture up to a particular temperature; after using $N_2$ bubbling to remove the ethanol reactant, continuing stirring for a predetermined duration of time, and then washing with hot chlorobenzene, washing twice with isooctane, then drying by $N_2$ to obtain a carrier. Alternatively, the preparation can be done in accordance with another example: successively adding $TiCl_4$, titanium tetraethoxide, magnesium ethoxide and o-cresol in chlorobenzene with stirring; adding ethanol and keeping stirring at high temperature for 3 h until magnesium ethoxide is dissolved; hot filtering and washing with warm chlorobenzene and then with isooctane, finally drying by $N_2$.

According to another method, magnesium alkoxide or magnesium chloroalkoxide are reacted with an excess of $TiCl_4$ in a solution containing the ring-substituted ether-acid ester compounds represented by the general formula (I)-(V) at a temperature of 80-135° C. According to a preferred method, the titanium compound represented by the general formula $TiX_n(OR)_{4-n}$, wherein R is $C_1$-$C_{20}$ hydrocarbon group, X is halogen, n=1-4; preferably $TiCl_4$, is reacted with the adduct represented by the formula $MgCl_2.mROH$ to prepare a solid catalyst component, wherein m is a number from 0.1 to 6, preferably from 2 to 3.5, and R is a hydrocarbon group having 1 to 20 carbon atoms. The adduct can be suitably prepared to be spherically shaped according to the following method: in the presence of an inert hydrocarbon which is immiscible with the adduct, alcohol and magnesium chloride are mixed, followed by quickly cooling the emulsion to solidify the adduct in the form of spherical particles. Examples of the spherical $MgCl_2.mROH$ adduct prepared according to the method can be found in U.S. Pat. No. 4,399,054 and in U.S. Pat. No. 4,469,648. The obtained adduct can be directly reacted with the Ti compound or it can be first subjected to thermal controlled dealcoholation (80-130° C.) to obtain an adduct in which the mole number of alcohol is generally lower than 3, preferably between 0.1 and 2.5. The adduct (dealcoholated or itself) can then be suspended in cold $TiCl_4$ (generally −25-0° C.) to react with the titanium compound; the mixture was heated to 80-130° C. and kept at this temperature for 0.5-2 hours. Treatment with $TiCl_4$ can be repeated one or more times. During the treatment with $TiCl_4$, the ring-substituted ether-acid ester compounds represented by the general formula (I)-(V) may be added and this treatment can be repeated one or more times.

Another method for preparing the solid catalyst component of the present invention includes steps as follows: anhydrous magnesium chloride and the ring-substituted ether-acid ester compounds represented by the general formula (I)-(V) are grinded together under a condition that activation of the magnesium dichloride occurs. The product thus obtained can be treated with an excess of $TiCl_4$ at a temperature of 80-130° C. one or more times. After the above treatment the product is washed with a hydrocarbon solvent until no chlorine ions exist. According to a further method, the product obtained by co-grinding anhydrous magnesium dichloride, titanium compound and the ring-substituted ether-acid ester compounds represented by the general formula (I)-(V) is treated with a halogenated hydrocarbon such as 1,2-dichloro ethane, chlorobenzene, methylene chloride or the like. This treatment is carried out at a temperature from 40° C. to boiling point of the halogenated hydrocarbon for 1-4 hours. Then the product can be obtained generally by washing with an inert hydrocarbon solvent such as hexane.

According to another method, magnesium dichloride is preactivated according to a well known method, and then treated with an excess of $TiCl_4$ at a temperature of about 80-135° C., wherein the solution contains ring-substituted ether-acid ester compounds represented by the general formula (I)-(V). The solid is treated with $TiCl_4$ repeatedly and washed with hexane to remove any unreacted $TiCl_4$.

A further method comprises the preparation carried out with reference to the preparation of titanium-containing solid catalyst component as disclosed in CN1208045: in the presence of one compound selected from alcohols, phenols, ketones, aldehydes, ethers, amines, pyridine and esters, a liquid magnesium compound is contacted with the liquid titanium compound to precipitate a solid at a low temperature, the temperature of contact is usually at −70-200° C., preferably −30-130° C., during contact, a ring-substituted ether-acid ester compounds represented by the general formula (I)-(V) is added for treatment.

Another method of the solid catalyst component of the present invention comprises: a magnesium compound is dissolved in a solvent system consisting of an organic epoxy compound, organophosphorus compound and an inert diluent composition to form a homogeneous solution, which is mixed with the titanium compound to precipitated a solid in the presence of co-precipitation agent; the solid is treated with a ring-substituted ether-acid ester compound represented by the general formula (I)-(V) to allow the ring-substituted ether-acid ester compound to load on the solid, if necessary, the thus-obtained product is then treated with titanium tetrahalide and an inert diluent, wherein the co-precipitating agent is one of organic acid anhydride, organic acid, ether and ketone. Among the components, based on per mol of magnesium halide, organic epoxy compound is 0.2 to 10 mol, organophosphorus compound is 0.1 to 3 mol, co-precipitation agent is 0.03 to 1.0 mol, halides and derivatives of transition metal Ti are 0.5 to 150 mol.

The solid catalyst component of the present invention can also be prepared by using an inorganic oxide, such as $SiO_2$, alumina or the porous resin, which is preloaded with a magnesium compound as a carrier, and activated by known methods, and then treating the loaded carrier with an excess of $TiCl_4$ at a temperature of about 80-135° C., wherein a ring-substituted ether-acid ester compounds represented by the general formula (I)-(V) is added during treatment.

The above reactions result in the formation of magnesium halide in an active form (normal crystalline magnesium halide has a regular structure, and can only load a small amount of Ti, thus having low activity. To prepare high activity loaded catalyst, magnesium halide must undergo activating treatment. The activating treatment includes using physical and/or chemical methods to turn the magnesium halide into microcrystalline, such that the active centers are located on the surface, edges and defects of magnesium halide. The treated magnesium halide microcrystalline suitable for loading Ti is considered "active magnesium halide"). In addition to these reactions, there are other well known methods in the literature which start with a compound different from the magnesium halide to form magnesium halide in an active form.

In any preparation methods, the ring-substituted ether-acid ester compounds represented by the general formula (I)-(V) can be directly added or obtained through an optional manner, for example, by use of appropriate precursors to prepare in situ, the appropriate precursors can complete the conversion in the presence of suitable electron donor compounds, for example, by esterification, transesterification etc. known chemical reactions. Typically, $MgCl_2$ and ring-substituted ether-acid ester compounds represented by the general formula (I)-(V) are used in the molar ratio of 0.01-5, preferably 0.05-2.0.

The solid catalyst component of the present invention is converted into a catalyst for olefin polymerization by reaction with an organic aluminum compound according to known methods. In particular, one object of the present invention is to provide a catalyst for olefin $CH_2$=CHR polymerization, wherein R is hydrogen or a hydrocarbon group having 1-12 carbon atoms, the catalyst comprising the reaction product of the following materials:

(a) a solid catalyst component of the present invention comprising Mg, Ti and a halogen and a ring-substituted ether-acid ester compound represented by a compound having the general formula (I)-(V);

(b) at least one organic aluminum compound of the general formula $AlR_nX_{(3-n)}$, wherein R is hydrogen or a hydrocarbon group having 1-20 carbon atoms; X is halogen, n is an integer of 0≤n≤3; and optionally, (c) at least one external electron donor compound.

Preferably, the organoaluminum compound (b) is selected from the group consisting of trialkylaluminum compound such as trimethylaluminum, triethylaluminum, triisobutylaluminum, tri-n-butyl aluminum, tri-n-hexyl aluminum, trioctyl aluminum. It is also possible to use trialkylaluminum and alkylaluminum halide, or a mixture of alkylaluminum sesquichloride such as $AlEt_2Cl$ and $Al_2Et_3Cl_3$, alkylalumoxanes can also be used.

For applications where good isotacticity is required, an external electron donor compound can be used. The external electron donor is selected from siloxane compounds represented by general formula $R_nSi(OR_1)_{4-n}$, wherein R and $R_1$ are $C_1$-$C_{18}$ hydrocarbon group, which may optionally be substituted by heteroatoms; n is an integer of 0≤n≤3.

Said specific silane compounds may be: trimethylmethoxysilane, trimethyl ethoxysilane, tri-n-propylmethoxysilane, tri-n-propylethoxysilane, tri-n-butylmethoxysilane, triisobutylethoxysilane, trihexylmethylsilane, trihexylethoxysilane, dimethyldimethoxysilane, dimethyldiethoxysilane, di-n-propyldimethoxysilane, diisopropyldimethoxysilane, di-n-propyldiethoxysilane, diisopropyldiethoxysilane, di-n-butyldiethoxysilane, diisobutyldiethoxysilane, di-tert-butyldimethoxysilane, di-tert-butyldimethoxysilane, di-n-butyldimethoxysilane, diisobutyldimethoxysilane, di-tert-butyldiethoxysilane, di-n-butyldiethoxysilane, n-butylmethyldimethoxysilane, di(2-ethylhexyl)dimethoxysilane, di(2-ethylhexyl)diethoxysilane, dicyclohexyldimethoxysilane, dicyclohexyldiethoxysilane, dicyclopentyldimethoxysilane, dicyclopentyldiethoxysilane, cyclohexylmethyldimethoxysilane, cyclohexylmethyldiethoxysilane, cyclohexylethyldimethoxysilane, cyclohexylisopropyldimethoxysilane, cyclohexylethyldiethoxysilane, cyclopentylmethyldimethoxysilane, cyclopentylethyldiethoxysilane, cyclopentylisopropyldiethoxysilane, cyclopentylisobutyldimethoxysilane, cyclohexyln-propyldimethoxysilane, cyclohexyln-propyldiethoxysilane, cyclohexyln-butyldiethoxysilane, pentylmethyldimethoxysilane, pentylmethyldiethoxysilane, pentylethyldimethoxysilane, pentylethyldiethoxysilane, cyclohexyldimethylmethoxysilane, cyclohexyldiethylmethoxysilane, cyclohexyldiethylmethoxysilane, cyclohexyldiethylethoxysilane, 2-ethylhexyltrimethoxysilane, cyclohexyldimethoxysilane, cyclohexyldiethoxysilane, 2-ethylhexyltriethoxysilane, ethyltrimethoxysilane, ethyltriethoxysilane, n-propyltrimethoxysilane, n-propyltriethoxysilane, isopropyltrimethoxysilane, isopropyltriethoxysilane, n-butyltrimethoxysilane, isobutyltrimethoxysilane, tert-butyltrimethoxysilane, n-butyltriethoxysilane, cyclohexyltrimethoxysilane, cyclohexyltriethoxysilane, cyclopentyltrimethoxysilane, cyclopentyltriethoxysilane, vinyltrimethoxysilane, vinyltriethoxysilane, 2-ethylhexyltrimethoxysilane, 2-ethylhexyltriethoxysilane, pentyltrimethoxysilane, pentyltriethoxysilane, tetramethoxysilane, tetraethoxysilane, cyclohexylcyclopentyldimethoxysilane, cyclohexylcyclopentyldiethoxysilane, cyclohexylcyclopentyldipropoxysilane, 3-methylcyclohexylcyclopentyldimethoxysilane, 4-methylcyclohexylcyclopentyldimethoxysilane, 3,5-dimethylcyclohexylcyclopentyldimethoxysilane, 3-methylcyclohexylcyclohexyldimethoxysilane, di(3-methylcyclohexyl)dimethoxysilane, 4-methylcyclohexylcyclohexyldimethoxysilane, di(4-methylcyclohexyl)dimethoxysilane, 3,5-dimethylcyclohexylcyclohexyldimethoxysilane, di(3,5-dimethylcyclohexyl)dimethoxysilane, tetrapropoxysilane, tetrabutoxysilan. The preferable compound among these organosilicon compounds are: di-n-propyldimethoxysilane, diisopropyldimethoxysilane, di-n-butyldimethoxysilane, diisobutyldimethoxysilane, di-tert-butyldimethoxysilane, di-n-butyldiethoxysilane, tert-butyltrimethoxysilane, dicyclohexyldimethoxysilane, dicyclohexyldiethoxysilane, cyclohexylmethyldimethoxysilane, cyclohexylethyldiethoxysilane, cyclohexylethyldimethoxysilane, cyclohexylethyldiethoxysilane, cyclopentylmethyldimethoxysilane, cyclopentylmethyldiethoxysilane, cyclopentylethyldimethoxysilane, cyclohexylcyclopentyldimethoxysilane, cyclohexylcyclopentyldiethoxysilane, 3-methylcyclohexylcyclopentyldimethoxysilane, 4-methylcyclohexylcyclopentyl dimethoxy silane and 3,5-dimethylcyclopentyldimethoxysilane, etc. These compounds C can be used alone or in combination.

Preferred examples of silicon compounds are cyclohexylmethyl dimethoxysilane; diisopropyl dimethoxysilane; di-n-butyl dimethoxysilane; diisobutyl dimethoxysilane; diphenyl dimethoxysilane; phenyltriethoxysilane; methyl tert-butyl dimethoxysilane; di cyclopentyl dimethoxysilane; 2-ethylpiperidin-2-t-butyl-dimethoxysilane and (1,1,1-trifluoro-2-propyl)-2-ethylpiperidine dimethoxysilane and (1,1,1-trifluoro-2-propyl)-methyldimethoxysilane, cyclohexyl trimethoxysilane; tert-butyl trimethoxysilane and tert-hexyl trimethoxysilane.

The catalysts of the present invention can be used for olefin $CH_2$=CHR (co)polymerization, wherein the olefin is ethylene, propylene, 1-butene, 4-methyl-1-pentene, 1-hexene or 1-octene.

In order to use the catalysts of the present invention for olefin polymerization, the catalyst prepared by component a, b, c can be used for both homo-polymerization and co-polymerization. Typically, the molar ratio of component b to component a is 1-1000 mol per mol of titanium atom contained in the component a, preferably 50-800 mol per mol of titanium atom contained in the component a; and the molar ratio of component c to component a is 0.002-10, preferably 0.01-2, more preferably 0.01-0.5.

The addition order of the components is arbitrary. Preferably, component b is firstly added to the polymerization system, and then component C, and component a is added last.

The polymerization process of the present invention can be carried out in the presence or absence of a solvent. Olefin monomers may be gaseous or liquid phase. Hydrogen can be further added as a molecular weight modifier. Of course, the polymerization can also be carried out in the absence of molecular weight modifier. The polymerization temperature is no greater than 200° C., preferably is between 20-100° C., and more preferably between 40-80° C. The polymerization pressure is no more than 10 MPa, and is preferably between 1-5 MPa. Both continuous polymerization and batch polymerization process can be used. The polymerization reaction can be divided into one, two or more stages.

The olefins to be homopolymerized or copolymerized using the catalyst of the present invention include linear olefins: ethylene, propylene, 1-butene, 1-pentene, 1-hexene, 1-heptene, 1-nonene, 1-decene; branched olefins such as: 3-methyl-1-butene and 4-methyl-1-pentene; dienes such as: butadiene, vinyl cyclopentene and vinyl cyclohexene. The catalyst of the present invention is preferably used for polymerization of polyethylene and polypropylene. These olefins may be used alone or in combination.

In terms of the olefin polymerization conducted by using the catalyst component a, b, c of the present invention (hereinafter referred to as the main polymerization), prepolymerization is recommended to increase the activity of the catalysts as well as the isotacticity, particle properties and of the productpolymers. The prepolymerization can also be used for styrene homopolymerization.

In the prepolymerization process, the addition order of each component and monomer is arbitrary. Preferably the component b is firstly added to the system containing an inert gas or olefins to be polymerized, and then one or more olefins to be polymerized are added after addition of component a. In the process of olefin prepolymerization using organosilane, it is recommended that component b is added to the polymerization system of an inert gas or olefins to be polymerized, followed by the addition of component c, which is then followed by the addition of component a, and the olefins are added last.

The present invention utilizes polyfunctional compounds having a specific structure, i.e., ring compounds as shown in the general formula (I) containing an ether bond and an ester bond, since the oxygen of the ether bond and the ester bond has a strong coordination effect and is relatively stable during the preparation of the catalyst, therefore playing an positive and effective role in the activity and isotacticity of the catalysts. And the same compound containing both ether bond and ester bond can have the advantages of two different functional groups and play a positive role especially in the regulation of the catalyst activity and control of polymer structure.

The specific ring-substituted structure of the compounds of the present invention has a steric effect and can dictate the stereo-configuration of ether and ester functional groups, thus having a positive effect in the formation of the catalyst active sites and improvement of the stereospecificity of the catalyst.

The present inventors have found in experiments that, when these compounds are used as an electron donor to prepare a Ziegler-Natta catalyst component, the catalyst component has an excellent activity and a polymer product having a high isotacticity can be obtained. The compounds of the invention are applied to several most representative Ziegler-Natta catalyst preparation systems including magnesium ethylate system, magnesium chloride alcoholate system and magnesium chloride dissolution and precipitation system and other major systems, respectively, the resulting catalysts have a high compound content, indicating that the compounds have good coordination performance and stability; the resulting catalysts are generally higher in activity than the catalysts prepared using traditional aromatic diester electron donor under the same conditions, and have a high stereospecificity.

SPECIFIC MODES FOR CARRYING OUT THE EMBODIMENTS

The following examples further illustrating the present invention are intended to make the advantages and effects of the invention better understood, but these examples are only for illustrating the present invention and not for limiting the present invention.

Five-membered ring ether ester compounds listed in the examples are only to illustrate the present invention, and not limiting the present invention. Other compounds that are within the scope of the present invention but not mentioned in the examples, such as the six-membered ring and seven-membered ring ether ester compounds, will also have similar properties as those of compounds of the examples.

Preparation of Ring-Substituted Ether-Acid Ester Compounds

Example 1 Synthesis of 9-methoxymethyl-fluorene carboxylic acid-(9)-methyl ester Step A: to a 1000 mL three-necked flask were successively added 18 g sodium hydride, 50 g fluorene, 150 mL toluene under nitrogen, with mechanical stirring, the temperature was raised to 125° C. to reflux for 4 h; after cooling to 90° C., 146.1 g diethyl carbonate was slowly added dropwise to the flask over 1.5 h, then the reaction was continued for 3 h; after cooling to 20° C., a mixture of 60 g concentrated hydrochloric acid and 75 g water was slowly added dropwise, and the temperature was controlled to be no greater than 40° C.; the organic phase was separated by filtering and washed with water to neutral, followed by rotary evaporation to yield a red-brown liquid; the resulting liquid obtained by rotary evaporation, 157.4 g acetic acid and 63 g 10% hydrochloric acid were refluxed overnight; the mixture was cooled to 20° C., followed by liquid separation; 30% NaOH solution was added to the organic phase after rotary evaporation, which was adjusted to pH 8 and extracted with ethyl acetate, the aqueous phase was retained. Concentrated hydrochloric acid was added to the aqueous phase to adjust the pH to 5, which was extracted with ethyl acetate, the organic phase was retained for rotary evaporation; the products were dissolved in ethyl acetate and frozen for recrystallization; the crude products after filtration were washed with hexane to give colorless crystals of about 10 g, melting point: 228~230° C.

Step B: to a 250 mL three-necked flask were added 2 g (9.5 mmol) 9-fluorene carboxylic acid, methanol (30 mL), concentrated sulfuric acid (0.2 mL); the mixture was heated to reflux for 2 h, cooled to room temperature, and poured into a saturated sodium bicarbonate solution, and extracted twice with ethyl acetate (30 mL*2), the combined organic phase was washed with brine (30 mL*1), evaporated under reduced pressure to give a yellow solid, followed by drying with oil pump to give 1.8 g crude products with mp 62-65° C.

Step C: to a 250 mL three-necked round bottom flask were added methanol (20 mL), metallic sodium (0.12 g, 5 mmol) and placed under ice-bath, after metallic sodium was completely dissolved until no bubble emerges, 9-fluorene carboxylic acid methyl ester (0.56 g, 2.5 mmol) was added and completely dissolved, the mixture appeared yellow and was stirred for 5 min, chloromethyl methyl ether (0.6 g, 7.5 mmol) was added therein, stirred for 30 min, poured into an aqueous solution, extracted with dichloromethane (20 mL*2) and extracted twice with ethyl acetate (50 mL*2). The combined organic phases were washed with saturated brine (50 mL*1), followed by rotary evaporation to remove liquid, the resulting crude product was washed with hexane to give the product, 126-129° C. 9-methoxymethyl-fluorene carboxylic acid-(9)-methyl ester, 1H-NMR (CDCl$_3$) δ (ppm): 3.370 (s, 3H, ether methyl), 3.660 (s, 3H, ester methyl), 3.791 (s, 2H, methylene hydrogen), 7.313-7.345 (t, 2H, aromatic hydrogen), 7.408-7.440 (t, 2H, aromatic hydrogen), 7.707-7.745 (m, 4H, aromatic hydrogen).

Example 2 Synthesis of 9-ethoxymethyl-fluorene carboxylic acid-(9)-n-butyl ester The synthetic steps were the same as those of Example 1, except that the methanol Step B was replaced by n-butanol.

1H-NMR (CDCl$_3$) δ (ppm): 0.86 (t, 3H, hydrogen), 1.27 (m, 2H, methylene hydrogen), 1.54 (m, 2H, methylene hydrogen), 3.37 (s, 3H, ether methyl hydrogen), 3.80 (s, 2H, ether, methylene hydrogen), 4.11 (t, 2H, ester methylene hydrogen), 7.31-7.40 (t, 2H, aromatic hydrogen), 7.42-7.43 (t, 2H, aromatic hydrogen), 7.72-7.74 (m, 4H, aromatic hydrogen).

Example 3 Synthesis of 9-methoxymethyl-fluorene carboxylic acid-(9)-isobutyl ester The synthetic steps were the same as those in Example 1, except that the methanol of step B was replaced by isobutanol. 1H-NMR (CDCl$_3$) δ (ppm): 0.832-0.0845 (d, 6H, methyl hydrogen), 1.833-1.900 (m, 1H, methine hydrogen), 3.384 (s, 3H, ether methyl hydrogen), 3.821 (s, 2H, ether methylene hydrogen), 3.887-3.900 (d, 2H, ester methylene hydrogen), 7.260-7.352 (t, 2H, aromatic hydrogen), 7.408-7.440 (t, 2H, the aromatic ring hydrogen), 7.735-7.750 (m, 4H, aromatic hydrogen).

Example 4 Synthesis of 9-methoxymethyl-fluorene carboxylic acid-(9)-isopropyl ester The synthetic steps were the same as those of Example 1, except that the methanol of step B was replaced by isopropanol. 1H-NMR (CDCl$_3$) δ (ppm): 1.179-1.191 (d, 6H, methyl hydrogen), 3.364 (s, 3H, ether methyl hydrogen), 3.768 (s, 2H, ether methylene hydrogen), 5.035-5.085 (m, 1H, methine hydrogen), 7.303-7.335 (t, 2H, aromatic hydrogen), 7.392-7.409 (t, 2H, aromatic hydrogen), 7.716-7.733 (m, 4H, aromatic ring hydrogen).

Example 5 Synthesis of 9-methoxymethyl-fluorene carboxylic acid-(9)-ethyl ester Synthetic steps were the same as those of Example 1, except that the methanol of step B was replaced by ethanol. 1H-NMR (CDCl$_3$) δ (ppm): 1.17-1.20 (t, 3H, methyl hydrogen), 3.37 (s, 3H, hydrogen methyl ether), 3.791 (s, 2H, ether methylene hydrogen), 4.14-4.19 (m, 2H, ester methylene hydrogen), 7.26-7.42 (t, 2H, aromatic hydrogen), 7.42-7.44 (t, 2H, aromatic hydrogen), 7.73-7.74 (m, 4H, aromatic ring hydrogen).

Example 6 Synthesis of 9-ethoxymethyl-fluorene carboxylic acid-(9) methyl ester The synthetic steps were the same as those of Example 1, except that the chloromethyl methyl ether of step C of was replaced by chloromethyl ether. 1H-NMR (CDCl$_3$) δ (ppm): 1.11-1.18 (t, 3H, ether methyl hydrogen), 3.40-3.46 (m, 2H, ether methylene hydrogen), 3.66 (s, 3H, ester methyl hydrogen), 3.65-3.79 (s, 2H, ether methylene hydrogen), 7.31-7.34 (t, 2H, aromatic hydrogen), 7.40-7.44 (t, 2H, aromatic hydrogen), 7.70-7.74 (m, 4H, aromatic hydrogen).

Example 7 Synthesis of 9-ethoxymethyl-fluorene carboxylic acid-(9)-ethyl ester The synthetic steps were the same as those of Example 1, except that the methanol of step B was replaced by ethanol, and chloromethyl methyl ether of Step C was replaced by chloromethyl ether. 1H-NMR (CDCl$_3$) δ (ppm): 1.13-1.17 (t, 3H, ether methyl hydrogen), 1.30-1.34 (t, 3H, ester methyl hydrogen), 3.40-3.46 (m, 2H, ether methylene hydrogens), 3.90 (s, 2H, ether methylene hydrogen), 4.12-4.16 (m, 2H, ester methylene hydrogen), 7.26-7.40 (t, 2H, aromatic hydrogen), 7.41-7.43 (t, 2H, aromatic hydrogen), 7.72-7.74 (m, 4H, aromatic hydrogen).

Example 8 Synthesis of 1-benzyloxymethyl-1-methoxyacyl-2,5-cyclopentadiene

The synthetic step was the same as Step c of Example 1, except that the chloromethyl methyl ether of Step C was replaced by chloromethyl benzyl ether, and 9-fluorene carboxylic acid methyl ester was replaced by cyclohexa-2,5-diene-carboxylic acid methyl ester. 1H-NMR (CDCl$_3$) δ (ppm): 2.62-2.64 (m, 1H, cyclohexadiene hydrogen), 3.63-3.67 (s, 3H, ester methyl hydrogen), 3.77-3.79 (s, 2H, ether methylene hydrogen), 4.60-4.66 (s, 2H, ether methylene hydrogen), 3.90 (s, 2H, ether methylene hydrogen), 5.58-5.62 (d, 2H, cyclohexadiene hydrogen), 5.64-5.70 (m, 2H, cyclohexadiene hydrogen), 7.16-7.20 (m, 5H, aromatic hydrogen).

Preparation of Solid Catalyst Component

Preparation of the catalysts in Examples was carried out in the protective atmosphere of high purity nitrogen. Specific examples were provided as follows.

Example 9

To a 500 ml fully nitrogen-purged five-necked flask equipped with a stirrer were added 10 g diethoxy magnesium and 80 mL toluene to prepare a suspension, and then 20 mL titanium tetrachloride was added dropwise at −15° C., after addition was completed the system was slowly warmed to 10° C. after 60 mL titanium tetrachloride was added dropwise, then slowly warmed to 80° C. and then, 2.8 g 9-methoxymethyl-fluorene carboxylic acid-(9)-methyl ester was added, and then the temperature of the system was raised up to 120° C. and maintained constant for 2 hours, then the liquid was cleaned by filter pressing and filtered, the resulting solid was washed 3 times with 120 mL titanium tetrachloride at 125° C. The resulting solid was washed two times at 60° C. and two times at room temperature with 150 mL hexane; after removal of the liquid by filtration and drying the solid, 10.43 g solid powder, i.e. solid catalyst component, was obtained. Analytical results of the solid showed that the titanium content was 3.90 (wt) %, fluorene ether ester content was 16.27 (wt) %.

Example 10

To a 500 ml fully nitrogen-purged five-necked flask equipped with a stirrer were added 10 g MgCl$_2$.2.5C$_2$H$_5$OH microspheres and 150 mL titanium tetrachloride to prepare a suspension, and then the system was kept at −15° C. for 1 hour and warmed to 80° C., 1.5 g 9-methoxymethyl-fluorene carboxylic acid-(9)-methyl ester was added, and then the system continued to warm up to 110° C. and maintained the temperature constant for 1 hour, then the liquid was cleaned by filter pressing and filtered, the resulting solid was washed 3 times with 120 mL titanium tetrachloride at 125° C. The resulting solid was washed four times with 150 mL hexane at 60° C., after filtering to remove the liquid and drying the solid, 5.61 g solid powder was obtained, i.e. solid catalyst component. Analytical results of the solid component showed that the titanium content was 3.23 (wt) %, fluorene ether ester content was 23.7 (wt) %.

Example 11

7.1 g anhydrous magnesium chloride, 38 mL decane and 35 mL 2-ethylhexanol were reacted at 130° C. for 2 hours to form a homogeneous solution. 1.7 g phthalic anhydride was added to the solution, and stirred for 1 hour at 130° C. to completely dissolve phthalic anhydride in the homogeneous solution. The resulting homogeneous solution was cooled to room temperature and was dropwise added to 200 mL titanium tetrachloride kept at −20° C. over 1 hour; After addition was completed, the mixed solution was heated to 110° C. over 4 hours, when the temperature reached 110° C., 5 g 9-methoxymethyl-fluorene carboxylic acid-(9)-methyl ester was added, the mixture was stirred at that temperature for 2 hours. After reaction, the solid portion was collected by hot filtration. The solid portion was suspended in 275 mL titanium tetrachloride and reacted at 110° C. for 2 hours. After the reaction, the solid was collected by hot filtration, sufficiently washed with decane and hexane at 110° C., followed by suction filtration to give a solid catalyst component. Analytical results of the solid component showed that the titanium content was 2.6 (wt) %, and the content of fluorene ether ester was 14.6 (wt) %.

Example 12

To a 500 ml fully nitrogen-purged five-necked flask equipped with a stirrer were added 10 g anhydrous magnesium chloride, 150 mL toluene, 17 mL epichlorohydrin and 16 mL tributyl phosphate at the room temperature, warmed to 50° C. with stirring and maintained for 2 hours until the solid was completely dissolved, and then 2.40 g phthalic anhydride was added, the reaction was maintained for 1 hour. The solution was cooled to −25° C., 110 mL titanium tetrachloride was dropwise added over 1 hour, the temperature was slowly raised to 80° C., in the heating process, the solid was precipitated stepwise. 5 g 9-methoxymethyl-fluorene carboxylic acid-(9)-methyl ester was added and the reaction was maintained at 80° C. for 1 hour. The resulting sold after filtration was washed twice with 200 mL toluene, and then 120 mL toluene and 80 mL titanium tetrachloride were added, the temperature was raised to 110° C. and maintained for 2 hours, then the liquid was cleaned by filter pressing, and the treatment was repeated one time. The resulting solid after filtration was washed one time with 100 mL dichloroethane, four times with hexane, and dried to give 10.2 g solid powder, i.e. the solid catalyst component. Analytical results of the solid component showed that the titanium content after analysis was 5.16 (wt) %, and the fluorene ether ester content was 17.46 (wt) %.

Examples 13-19

Preparation steps of catalyst component were the same as described in Example 9, except that the 9-methoxymethyl-fluorene carboxylic acid-(9)-methyl ester was replaced by 9-methoxy-fluorene carboxylic acid-(9)-n-butyl ester, 9-methoxy-methyl-fluorene carboxylic acid-(9)-isobutyl ester, 9-methoxy-fluorene carboxylic acid-(9)-isopropyl ester, 9-methoxy-methyl-fluorene carboxylic acid-(9)-ethyl ester, 9-ethoxymethyl-fluorene carboxylic acid-(9)-methyl ester, 9-ethoxymethyl-fluorene carboxylic acid-(9)-ethyl ester, or 1-benzyloxymethyl-1-methoxyacyl-2,5-cyclopentadiene, respectively.

Examples 20-26

Preparation steps of catalyst component were the same as described in Example 10, except that the 9-methoxymethyl-fluorene carboxylic acid-(9)-methyl ester was replaced by 9-methoxy-fluorene carboxylic acid-(9)-n-butyl ester, 9-methoxy-methyl-fluorene carboxylic acid-(9)-isobutyl ester, 9-methoxy-fluorene carboxylic acid-(9)-isopropyl ester, 9-methoxy-methyl-fluorene carboxylic acid-(9)-ethyl ester, 9-ethoxymethyl-fluorene carboxylic acid-(9)-methyl ester, 9-ethoxymethyl-fluorene carboxylic acid-(9)-ethyl ester, or 1-benzyloxymethyl-1-methoxyacyl-2,5-cyclopentadiene, respectively.

Examples 27-28

Preparation steps of catalyst component were the same as described in Example 11, except that the 9-methoxymethyl-fluorene carboxylic acid-(9)-methyl ester was replaced by 9-methoxy-fluorene carboxylic acid-(9)-n-butyl ester or 9-methoxy-fluorene carboxylic acid-(9)-ethyl ester, respectively.

Polymerization

Polymerization evaluation was made by using a solid catalyst as the catalyst component for olefin polymerization:

To a 5 L fully nitrogen-purged stainless steel reactor were added 5 mL solution of triethylaluminum in hexane at a concentration of 0.5 mol/L and 1 mL solution of methyl cyclohexyl dimethoxy silane (CMMS) in hexane at a concentration of 0.1 mol/L and 10 mg prepared catalyst, 10 mL hexane was added to rinse the feed lines, and then 2 L hydrogen (standard state) and 2.5 L purified propylene were added, the reaction was controlled at 20° C. to prepolymerize for 5 minutes, the temperature was raised to 70° C., and at this temperature the polymerization reaction was carried out for 1 hour. After the reaction, the reactor was cooled and the stirring was stopped, the reaction product was discharged and dried to obtain a polymer. (Bulk density of the polymer measured by JB/T 2412-2008 method, isotacticity measured by JB/T 3682-2000 method.)

TABLE 1

Catalyst performance

| Example No. | internal electron donor type | wt % | titanium wt % | Activity Kg/gCat · h$^{-1}$ | isotacticity % | Bulk density g/cm$^3$ |
|---|---|---|---|---|---|---|
| 9 | 9-methoxymethyl-fluorene carboxylic acid-(9)-methyl ester | 16.27 | 3.90 | 64.0 | 97.6 | 0.385 |
| 10 | 9-methoxymethyl-fluorene carboxylic acid-(9)-methyl ester | 23.7 | 3.23 | 76.7 | 98.0 | 0.353 |
| 11 | 9-methoxymethyl-fluorene carboxylic acid-(9)-methyl ester | 14.6 | 2.60 | 52.6 | 97.5 | 0.361 |
| 12 | 9-methoxymethyl-fluorene carboxylic acid-(9)-methyl ester | 17.46 | 5.16 | 45.8 | 97.2 | 0.380 |
| 13 | 9-methoxymethyl-fluorene carboxylic acid-(9)-n-butyl ester | 12.44 | 3.14 | 76.0 | 98.2 | 0.413 |
| 14 | 9-methoxymethyl-fluorene carboxylic acid-(9)-isobutyl ester | 11.00 | 2.10 | 49.0 | 98.0 | 0.396 |

TABLE 1-continued

Catalyst performance

| Example No. | internal electron donor type | internal electron donor wt % | titanium wt % | Activity Kg/gCat · h$^{-1}$ | isotacticity % | Bulk density g/cm$^3$ |
|---|---|---|---|---|---|---|
| 15 | 9-methoxymethyl-fluorene carboxylic acid-(9)-isopropyl ester | 7.28 | 4.05 | 52.0 | 97.9 | 0.373 |
| 16 | 9-methoxymethyl-fluorene carboxylic acid-(9)-ethyl ester | 16.92 | 3.34 | 52.0 | 98.0 | 0.382 |
| 17 | 9-ethoxymethyl-fluorene carboxylic acid-(9)-methyl ester | 21.32 | 2.66 | 55.0 | 98.4 | 0.373 |
| 18 | 9-ethoxymethyl-fluorene carboxylic acid-(9)-ethyl ester | 16.71 | 2.93 | 46.0 | 98.9 | 0.388 |
| 19 | 1-benzoxymethyl-1-methoxyacyl-2,5-cyclopentadiene | 10.20 | 3.25 | 32.0 | 97.1 | 0.387 |
| 20 | 9-methoxymethyl-fluorene carboxylic acid-(9)-n-butyl ester | 22.00 | 3.10 | 49.0 | 97.6 | 0.360 |
| 21 | 9-methoxymethyl-fluorene carboxylic acid-(9)-isobutyl ester | 13.60 | 2.68 | 55.7 | 97.5 | 0.403 |
| 22 | 9-methoxymethyl-fluorene carboxylic acid-(9)-isopropyl ester | 19.16 | 3.43 | 55.0 | 97.3 | 0.415 |
| 23 | 9-methoxymethyl-fluorene carboxylic acid-(9)-ethyl ester | 23.40 | 2.88 | 59.0 | 98.9 | 0.375 |
| 24 | 9-ethoxymethyl-fluorene carboxylic acid-(9)-methyl ester | 16.60 | 2.75 | 62.0 | 98.0 | 0.4028 |
| 25 | 9-ethoxymethyl-fluorene carboxylic acid-(9)-ethyl ester | 13.42 | 3.14 | 54.0 | 98.2 | 0.356 |
| 26 | 1-benzoxymethyl-1-methoxyacyl-2,5-cyclopentadiene | 13.22 | 3.51 | 35.0 | 97.7 | 0.379 |
| 27 | 9-methoxymethyl-fluorene carboxylic acid-(9)-n-butyl ester | 18.77 | 4.18 | 38.4 | 97.4 | 0.338 |
| 28 | 9-methoxymethyl-fluorene carboxylic acid-(9)-ethyl ester | 16.54 | 3.91 | 30.5 | 95.2 | 0.380 |

The polymerization results of the above table show that, using fluorenyl ether-acid ester selected from ring-substituted an ether-acid ester compounds as internal electron donor and using catalysts obtained according to four different catalyst preparation processes for propylene polymerization, high activity level can be achieved, and the polypropylene prepared under the standard polymerization conditions with the aid of methylcyclohexyl dimethoxysilane external electron donor has an isotacticity generally higher than 97%, indicating that the type of compounds can be used as the internal electron donor to be used in a variety of typical catalyst preparation routes, allowing the catalysts to have excellent performance for polymerization and obtain a high catalytic activity and a polypropylene product having high isotacticity.

Although the above has described the present invention with the general and specific embodiments in detail, on the basis of the present invention, it is obvious for those skilled in this art to make certain modifications or improvements. Therefore, these modifications or improvements made without departing from the spirit of the present invention belong to the scope of the invention as claimed.

INDUSTRIAL APPLICABILITY

The present invention provides a solid catalyst component for olefin polymerization, which comprises Mg, Ti, a halogen and an electron donor. The electron donor is selected from at least one of ring-substituted ether-acid ester compounds of the general formula (I). Also provided is a catalyst containing the solid catalyst component and the application of the catalyst in olefin polymerization reactions, particularly in the reaction of propylene polymerization. The compound with a specific ring-substituted structure contained in the solid catalyst component of the present invention has a steric hindrance effect and is capable of determining the spatial configuration of ether and acid ester functional groups, which has a positive influence on the formation of an active center of the catalyst and the improvement of the stereospecificity of the catalyst. The present invention has industrial applicability.

The invention claimed is:

1. A solid catalyst component for olefin polymerization, comprising an electron donor having the below structure

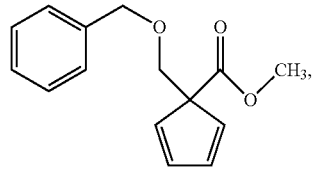 [SMILES: COC(=O)C1(COCc2ccccc2)C=CC=C1]

wherein the solid catalyst component is the reaction product of a magnesium compound, a titanium compound, and the electron donor, wherein the magnesium compound is selected from at least one of: Mg(OR)$_2$, X$_n$Mg(OR)$_{2-n}$, MgCl$_2$.mROH, R$_{2-n}$MgX$_n$, MgR$_2$, MgCl$_2$/SiO$_2$, MgCl$_2$/Al$_2$O$_3$, wherein m is a number from 0.1 to 6, 0<n<2, X is halogen, R is hydrogen or C$_1$-C$_{20}$ hydrocarbon group; and wherein the Ti compound is represented by the general formula TiX$_n$(OR')$_{4-n}$, wherein R' is C$_1$-C$_{20}$ hydrocarbon group, X is halogen, and n=1-4.

* * * * *